United States Patent
Dyne

(10) Patent No.: US 10,325,427 B2
(45) Date of Patent: Jun. 18, 2019

(54) SYSTEM AND METHOD FOR TRANSIT ACCESS USING EEG SENSORS

(71) Applicant: Cubic Corporation, San Diego, CA (US)

(72) Inventor: Mark Dyne, Croydon (GB)

(73) Assignee: Cubic Corporation, San Diego, CA (US)

( * ) Notice: Subject to any disclaimer, the term of this patent is extended or adjusted under 35 U.S.C. 154(b) by 0 days.

(21) Appl. No.: 16/019,242

(22) Filed: Jun. 26, 2018

(65) Prior Publication Data

US 2019/0005752 A1 Jan. 3, 2019

Related U.S. Application Data

(60) Provisional application No. 62/526,153, filed on Jun. 28, 2017.

(51) Int. Cl.
| | |
|---|---|
| *A61B 5/00* | (2006.01) |
| *A61B 5/16* | (2006.01) |
| *G06F 5/00* | (2006.01) |
| *G06K 5/00* | (2006.01) |
| *G07C 9/00* | (2006.01) |
| *H04W 4/80* | (2018.01) |

(Continued)

(52) U.S. Cl.
CPC ........ *G07C 9/00087* (2013.01); *A61B 5/0478* (2013.01); *A61B 5/04842* (2013.01);
(Continued)

(58) Field of Classification Search
CPC .......... G06K 5/00; G06Q 20/18; G06Q 20/32; G06Q 20/20; H04W 4/04; G07B 15/04; G07C 9/00
USPC ........................ 340/5.65, 5.28; 235/380, 382
See application file for complete search history.

(56) References Cited

U.S. PATENT DOCUMENTS

| | | | | |
|---|---|---|---|---|
| 5,837,982 A | * | 11/1998 | Fujioka | .............. G06K 7/10079 340/10.2 |
| 6,928,354 B2 | * | 8/2005 | Ryu | ........................ A61B 5/18 188/2 R |

(Continued)

FOREIGN PATENT DOCUMENTS

| | | |
|---|---|---|
| DE | 10329901 A1 | 1/2005 |
| EP | 2480359 A1 | 8/2012 |

OTHER PUBLICATIONS

International Search Report and Written Opinion dated Oct. 9, 2018 for International Patent Application No. PCT/US2018/039970, all pages.

*Primary Examiner* — Nam V Nguyen
(74) *Attorney, Agent, or Firm* — Kilpatrick Townsend & Stockton

(57) ABSTRACT

A wearable electronic device comprising an electroencephalography (EEG) sensor for enabling access to a transit system. The device may also include a device transmitter configured to wirelessly transmit a request signal to a gate receiver. The device may further include a device processor configured to receive an EEG signal from the EEG sensor, analyze the EEG signal to determine that the transit user is attempting to enter the transit system through a particular gate, generate the request signal identifying the transit user and indicating that the transit user is attempting to enter the transit system through the particular gate, and wirelessly transmit, using the device transmitter, the request signal to the gate receiver. The EEG signal may be based at least in part on the transit user viewing a visual stimuli displayed by the particular gate.

17 Claims, 12 Drawing Sheets

(51) Int. Cl.
    *A61B 5/048*     (2006.01)
    *G07B 15/02*     (2011.01)
    *H04L 29/08*     (2006.01)
    *A61B 5/0478*     (2006.01)
    *A61B 5/0484*     (2006.01)
    *G06F 3/01*     (2006.01)

(52) U.S. Cl.
    CPC ............ *A61B 5/165* (2013.01); *A61B 5/6803* (2013.01); *G06F 3/015* (2013.01); *G07B 15/02* (2013.01); *H04L 67/12* (2013.01); *H04L 67/325* (2013.01); *H04W 4/80* (2018.02); *A61B 5/048* (2013.01); *A61B 2503/12* (2013.01); *G07C 2009/00095* (2013.01)

(56) References Cited

U.S. PATENT DOCUMENTS

| | | | | |
|---|---|---|---|---|
| 8,095,209 B2* | 1/2012 | Flaherty | .................... | A61B 5/04 600/544 |
| 8,135,957 B2* | 3/2012 | Dinges | ............... | G06K 9/00885 713/186 |
| 8,988,350 B2* | 3/2015 | Karmarkar | .............. | G06F 3/013 345/158 |
| 9,317,976 B2* | 4/2016 | Andrews | ................ | G07B 15/00 |
| 9,501,768 B2* | 11/2016 | Ho | ........................ | G06Q 20/18 |
| 9,563,273 B2* | 2/2017 | Mann | ..................... | G06F 3/015 |
| 9,986,933 B2* | 6/2018 | Nutaro | ................ | A61B 5/0484 |
| 10,044,712 B2* | 8/2018 | Gordon | ............. | G02B 27/0172 |
| 10,149,958 B1* | 12/2018 | Tran | ..................... | A61M 21/00 |
| 10,152,838 B2* | 12/2018 | Einberg | ................. | B60R 25/24 |
| 2010/0234752 A1* | 9/2010 | Sullivan | ............ | A61B 5/04842 600/544 |
| 2013/0018705 A1* | 1/2013 | Heath | .................... | G08G 1/017 705/13 |
| 2013/0127708 A1* | 5/2013 | Jung | ................... | A61B 5/0006 345/156 |
| 2014/0023999 A1 | 1/2014 | Greder | | |
| 2015/0272496 A1* | 10/2015 | Klappert | ................ | A61B 5/486 600/545 |
| 2016/0042333 A1 | 2/2016 | Ho et al. | | |
| 2016/0060944 A1* | 3/2016 | Perkins | .................... | G07C 9/02 49/14 |
| 2017/0061715 A1* | 3/2017 | Busch-Sorensen | ......................... | G07C 9/00111 |

\* cited by examiner

SYSTEM AND METHOD FOR TRANSIT
ACCESS USING EEG SENSORS

CROSS-REFERENCES TO RELATED
APPLICATIONS

This Application claims priority to U.S. Provisional Patent Application No. 62/526,153 filed Jun. 28, 2017 titled "NEURO TICKET", the entire disclosure of which is hereby incorporated by reference, for all purposes, as if fully set forth herein.

BACKGROUND OF THE INVENTION

As populations in the world's largest city centers continue to grow, often at an exponential rate, public and private transportation systems are becoming increasingly burdened with increased ridership and transit stations are becoming increasingly congested, causing delays to transit users and increased costs to the transportation systems. The use of sophisticated mobile communication devices presents an appealing approach for managing such overcrowding. Unfortunately, existing devices and approaches are insufficient to alleviate these problems. Accordingly, new systems, methods, and other techniques are needed.

BRIEF SUMMARY OF THE INVENTION

A summary of the invention is described in reference to one or more examples listed below. As used below, any reference to a series of examples is to be understood as a reference to each of those examples disjunctively (e.g., "Examples 1-4" is to be understood as "Examples 1, 2, 3, or 4").

Example 1 is a wearable electronic device for enabling access to a transit system, the wearable electronic device comprising: an electroencephalography (EEG) sensor configured to detect an EEG signal corresponding to a transit user; a device transmitter configured to wirelessly transmit a request signal to a gate receiver; and a device processor configured to perform operations including: receiving the EEG signal from the EEG sensor; analyzing the EEG signal to determine that the transit user is attempting to enter the transit system through a particular gate; generating the request signal, wherein the request signal identifies the transit user and indicates that the transit user is attempting to enter the transit system through the particular gate; and wirelessly transmitting, using the device transmitter, the request signal to the gate receiver.

Example 2 is the wearable electronic device of example(s) 1, wherein the EEG signal corresponding to the transit user is based at least in part on the transit user viewing a visual stimuli displayed by the particular gate.

Example 3 is the wearable electronic device of example(s) 1-2, wherein analyzing the EEG signal to determine that the transit user is attempting to enter the transit system through the particular gate includes: determining a time range at which a visual stimuli displayed by the particular gate exhibits a decreased magnitude or an increased magnitude; determining a critical time at which the EEG signal exhibits a minimum magnitude or a maximum magnitude; and determining that the critical time is within the time range.

Example 4 is the wearable electronic device of example(s) 1-3, wherein analyzing the EEG signal to determine that the transit user is attempting to enter the transit system through the particular gate further includes: determining a second time range at which a second visual stimuli displayed by a second gate exhibits a second decreased magnitude or a second increased magnitude; and determining that the critical time is not within the second time range; wherein: the particular gate is a first gate; the time range is a first time range; the visual stimuli is a first visual stimuli; the decreased magnitude is a first decreased magnitude; and the increased magnitude is a first increased magnitude.

Example 5 is the wearable electronic device of example(s) 1-4, wherein the operations further include: receiving, from a first transmitter communicatively coupled to the first gate, the first time range; and receiving, from a second transmitter communicatively coupled to the second gate, the second time range.

Example 6 is the wearable electronic device of example(s) 1-5, wherein the operations further include: receiving, from a location transmitter communicatively coupled to the first gate and the second gate, the first time range and the second time range.

Example 7 is the wearable electronic device of example(s) 1-6, wherein the particular gate allows the transit user to access the transit system upon reception of the request signal.

Example 8 is a method of using EEG for enabling access to a transit system, the method comprising: receiving an EEG signal corresponding to a transit user from an EEG sensor; analyzing the EEG signal to determine that the transit user is attempting to enter the transit system through a particular gate; generating a request signal, wherein the request signal identifies the transit user and indicates that the transit user is attempting to enter the transit system through the particular gate; and wirelessly transmitting the request signal to a gate receiver.

Example 9 is the method of example(s) 8, wherein the EEG signal corresponding to the transit user is based at least in part on the transit user viewing a visual stimuli displayed by the particular gate.

Example 10 is the method of example(s) 8-9, wherein analyzing the EEG signal to determine that the transit user is attempting to enter the transit system through the particular gate includes: determining a time range at which a visual stimuli displayed by the particular gate exhibits a decreased magnitude or an increased magnitude; determining a critical time at which the EEG signal exhibits a minimum magnitude or a maximum magnitude; and determining that the critical time is within the time range.

Example 11 is the method of example(s) 8-10, wherein analyzing the EEG signal to determine that the transit user is attempting to enter the transit system through the particular gate further includes: determining a second time range at which a second visual stimuli displayed by a second gate exhibits a second decreased magnitude or a second increased magnitude; and determining that the critical time is not within the second time range; wherein: the particular gate is a first gate; the time range is a first time range; the visual stimuli is a first visual stimuli; the decreased magnitude is a first decreased magnitude; and the increased magnitude is a first increased magnitude.

Example 12 is the method of example(s) 8-11, further comprising: receiving, from a first transmitter communicatively coupled to the first gate, the first time range; and receiving, from a second transmitter communicatively coupled to the second gate, the second time range.

Example 13 is the method of example(s) 8-12, further comprising: receiving, from a location transmitter communicatively coupled to the first gate and the second gate, the first time range and the second time range.

Example 14 is the method of example(s) 8-13, wherein the particular gate allows the transit user to access the transit system upon reception of the request signal.

Example 15 is a non-transitory computer-readable medium comprising instructions that, when executed by a processor, cause the processor to perform operations comprising: receiving an EEG signal corresponding to a transit user from an EEG sensor; analyzing the EEG signal to determine that the transit user is attempting to enter a transit system through a particular gate; generating a request signal, wherein the request signal identifies the transit user and indicates that the transit user is attempting to enter the transit system through the particular gate; and wirelessly transmitting the request signal to a gate receiver.

Example 16 is the non-transitory computer-readable medium of example(s) 15, wherein the EEG signal corresponding to the transit user is based at least in part on the transit user viewing a visual stimuli displayed by the particular gate.

Example 17 is the non-transitory computer-readable medium of example(s) 15-16, wherein analyzing the EEG signal to determine that the transit user is attempting to enter the transit system through the particular gate includes: determining a time range at which a visual stimuli displayed by the particular gate exhibits a decreased magnitude or an increased magnitude; determining a critical time at which the EEG signal exhibits a minimum magnitude or a maximum magnitude; and determining that the critical time is within the time range.

Example 18 is the non-transitory computer-readable medium of example(s) 15-17, wherein analyzing the EEG signal to determine that the transit user is attempting to enter the transit system through the particular gate further includes: determining a second time range at which a second visual stimuli displayed by a second gate exhibits a second decreased magnitude or a second increased magnitude; and determining that the critical time is not within the second time range; wherein: the particular gate is a first gate; the time range is a first time range; the visual stimuli is a first visual stimuli; the decreased magnitude is a first decreased magnitude; and the increased magnitude is a first increased magnitude.

Example 19 is the non-transitory computer-readable medium of example(s) 15-18, wherein the operations further include: receiving, from a first transmitter communicatively coupled to the first gate, the first time range; and receiving, from a second transmitter communicatively coupled to the second gate, the second time range.

Example 20 is the non-transitory computer-readable medium of example(s) 15-19, wherein the operations further include: receiving, from a location transmitter communicatively coupled to the first gate and the second gate, the first time range and the second time range.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and various ways in which it may be practiced.

Figure 1:
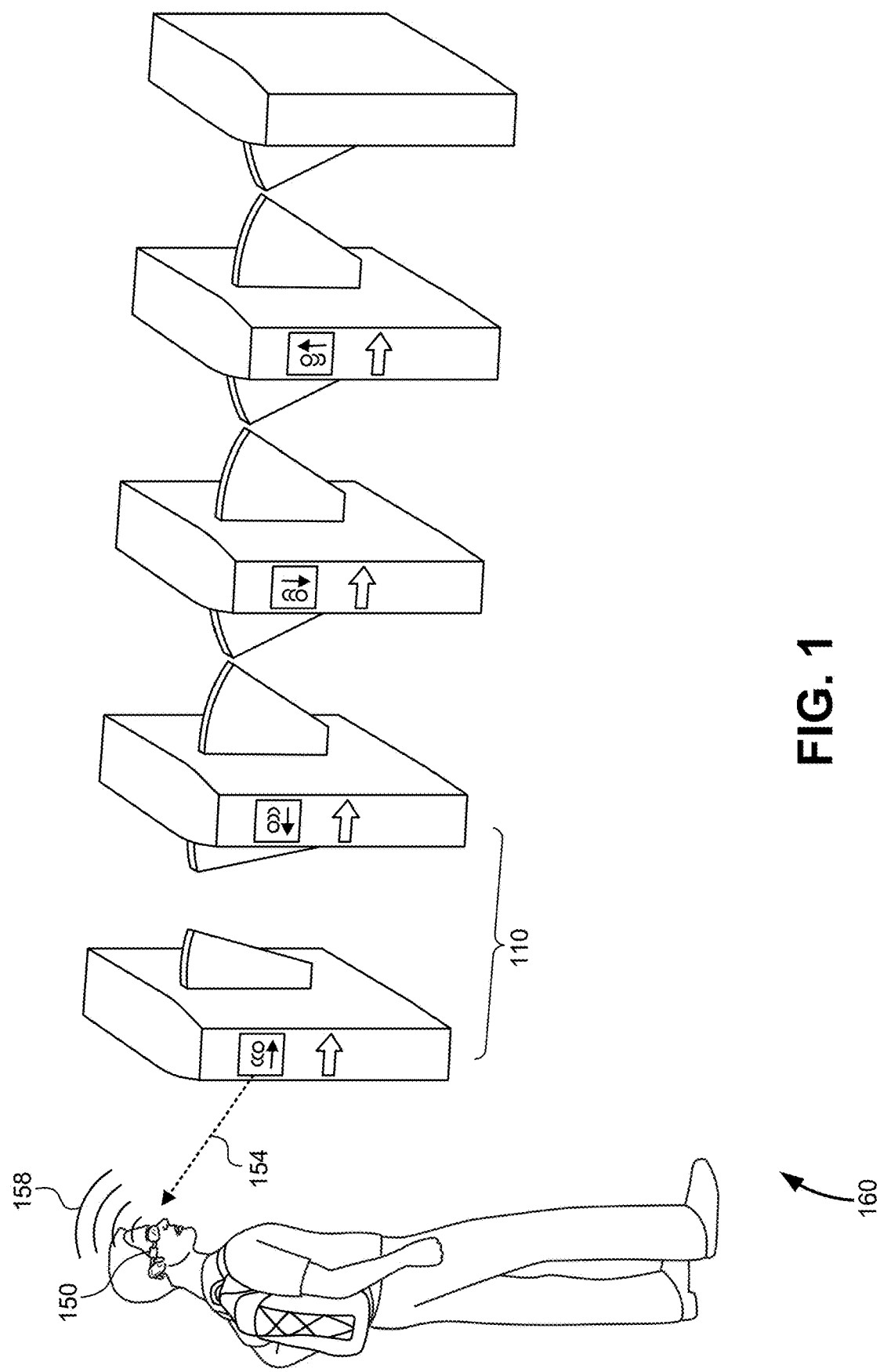
FIG. 1 illustrates a scene of a transit user gaining entry to a transit system at a transit location using a wearable electronic device, according to some embodiments of the present disclosure.

In the appended figures, similar components and/or features may have the same numerical reference label. Further, various components of the same type may be distinguished by following the reference label by a dash followed by a second numerical reference label that distinguishes among the similar components and/or features. If only the first numerical reference label is used in the specification, the description is applicable to any one of the similar components and/or features having the same first numerical reference label irrespective of the suffix.

DETAILED DESCRIPTION OF THE INVENTION

Systems, methods, and techniques are provided in the present disclosure for enabling transit access using electroencephalography (EEG) sensors. Embodiments described herein enable users' thoughts and mental processes to trigger the opening of a transit gate without the use of the users' hands by providing an interface between an EEG sensor and the transit gate. Although the embodiments described herein are directed toward use in transit, it will be understood that embodiments may be utilized in other applications, such as hands-free remote control of cameras, light switch operation, lift controller, raising an alarm or call for help, and the like.

Transit systems traditionally require a user to use his or her hands when accessing transit services, such as entering a subway station, bus, etc. A physical barrier such as a gate is typically opened by requiring some sort of manual interaction from a transit user, such as presenting a ticket, card, phone, etc. But this required interaction can have its drawbacks. For example, it can result in increased time at a gate while the user performs the manual interaction. This is especially true for transit users that may have some physical or other impairment that makes the manual interaction more difficult to perform.

Embodiments described herein address these and other concerns by providing an EEG device for controlling gate operation using, for example, a visual or audible stimulus. More specifically, a specific stimulus (or stimuli) may be located near a transit gate which, when viewed and/or heard by a transit user will form identifiable brain activity in the transit user. When this brain activity is read and identified by a device (e.g., an EEG device incorporated into glasses or some other wearable item) worn by the user, the device can send a wireless message (e.g. via Bluetooth low energy (BLE)) to the gate (when it is determined to be close enough to the gate). The gate can, using local and/or remote resources, identify the user based on the brain activity and/or device identifier, open the gate, and (when needed) charge an account of the user for transit services. Different gates can have different stimuli to ensure the correct gate is opened. Further, the field of vision of the stimuli may be limited to avoid miscalculations (e.g., situating or otherwise showing the stimuli in a way that reduces the likelihood that a user at a first gate might accidentally view the stimuli of a second gate and open the second gate by mistake).

In some embodiments, a transit user having a transit account with the transit system and wearing EEG-enabled glasses can approach a gate in the transit system. Upon viewing visual stimuli associated with that gate, the EEG-enabled glasses may identify brain activity associated with viewing the visual stimuli and transmit a BLE message to the gate. In some embodiments, an application programming interface (API) may be implemented within the glasses/wearable device which can communicate with a gate/station API layer that does the account checking and validation.

An example embodiment may proceed in the following manner. First, glasses (or similar EEG-enabled device) may identify brain activity associated with a specific visual stimulus corresponding to a particular transit gate. Second, the glasses may translate the information and send this information (e.g., via a call to an API layer) to a back-end system (which may be a server located in the gate, or a server located remotely), identifying the account ID and gate number. Third, the backend system may check account information and validity to travel. Fourth, the back-end system may send verification information (e.g., a success/error message) to the glasses. Fifth, the glasses may receive the verification information and transmit a BLE message to the gate when it is determined that it is close enough to the gate (e.g., when proximity, as measured by received signal strength indicator (RSSI), is within a certain threshold). Sixth, the gate may verify information in the BLE message (if needed) and then open the gate (e.g., remove a physical barrier), allowing the transit user to pass through. According to some embodiments, some or all messages can be encrypted and decrypted at each end of the communication.

In some embodiments, the back-end system may communicate directly with the gate after receiving information from the glasses, causing the gate to open (without a separate BLE message from the glasses to the gate). In some embodiments, the EEG-enabled device may analyze the brain activity associated with the specific visual stimulus to determine which gate corresponds to the visual stimulus. Embodiments described herein can provide a variety of advantages over traditional transit ticketing. In particular, embodiments herein can provide less able-bodied travelers more independence, reduce time at the gate and corresponding delays, free resources (such as station staff) for other tasks, and/or other such advantages.

FIG. 1 illustrates an example of the present invention in which a transit user gains entry to a transit system 100 at a transit location 160 using a wearable electronic device 150. In some embodiments, wearable electronic device 150 includes one or more EEG sensors that make physical contact with the transit user's head. As the transit user approaches gates 110, the transit user views visual stimuli 154 which causes a particular set of electrical activity in the transit user's brain. Wearable electronic device 150 may then detect an EEG signal related to the electrical activity. In some instances, wearable electronic device 150 may determine the identity of the transit user and the particular gate through which the transit user is attempting to enter transit system 100 based on the EEG signal. This information is wirelessly transmitted to gate 110 via a request signal 158 which may cause barriers positioned at gate 110 to be removed after verifying that the transit user is permitted to access transit system 100.

Although wearable electronic device 150 is depicted in FIG. 1 as being attached to the temple of a pair of glasses, wearable electronic device 150 may be implemented in a variety of ways. For example, wearable electronic device 150 may be integrated with the glasses or attached to any part of the glasses, such as the ear piece, the bridge, the rim, the top bar, etc. In some embodiments, wearable electronic device 150 is attached to or integrated with a hat or headband worn by the transit user. In some embodiments, wearable electronic device 150 is directly attached to the transit user using adhesive, suction, or another means of attachment.

Figure 2:
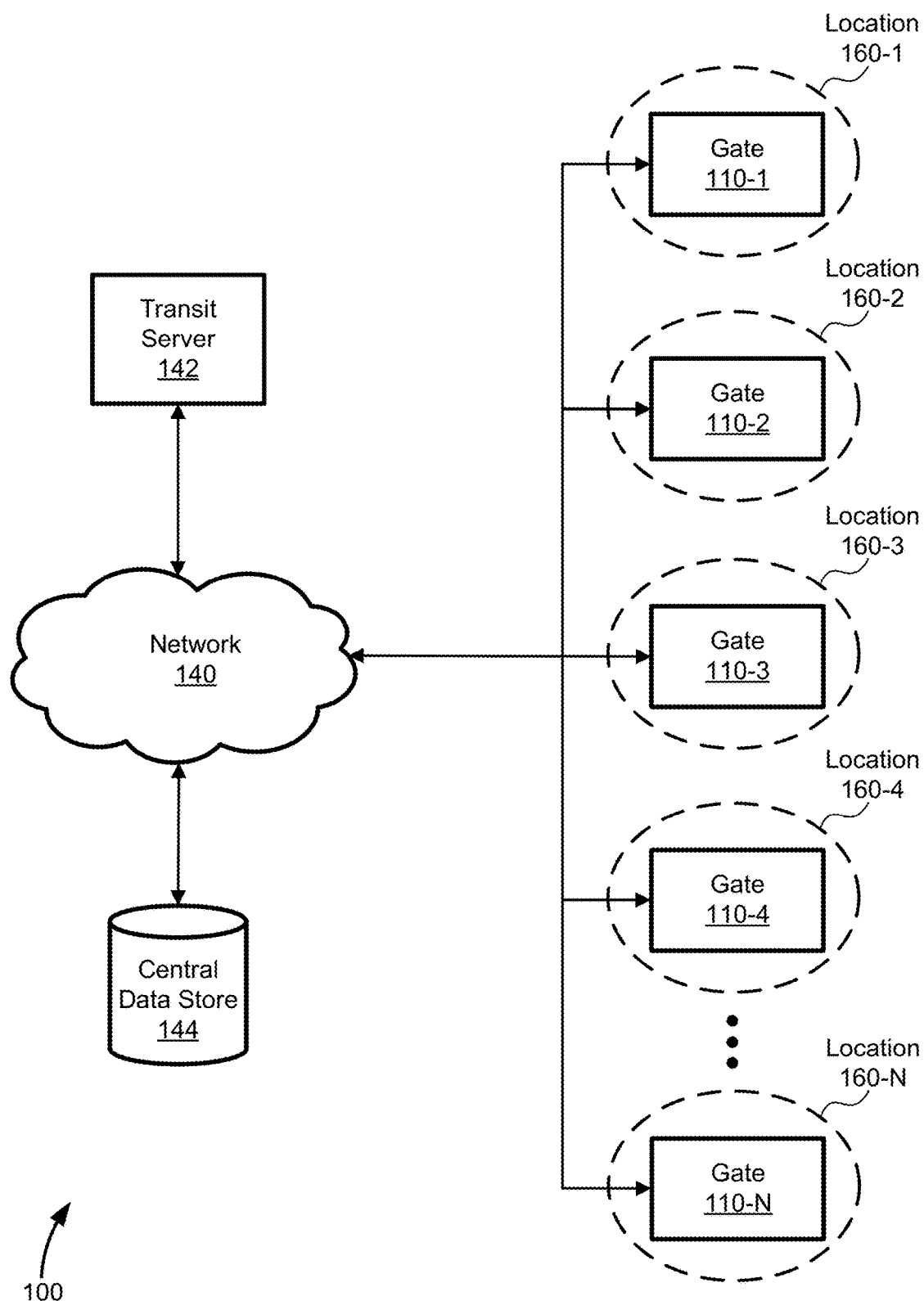
FIG. 2 illustrates a block diagram of a transit system, according to some embodiments of the present disclosure.

FIG. 2 illustrates a block diagram of transit system 100, according to some embodiments of the present disclosure. Transit system 100 may include a plurality of gates 110 located at a plurality of locations 160 (also referred to herein as transit locations 160). Each of locations 160 may include a non-restricted access area and a restricted access area. The non-restricted access area may include areas that are freely accessible to the general public, whereas the restricted access area may be reserved exclusively for customers of transit system 100. Examples of a restricted access area may include: the inside of a bus or train, a bus or train platform, the inside of a bus or train station, and the like. Each of locations 160 may include a single or multiple gates 110, and in some embodiments each of gates 110 may include an entry point that defines a passageway and separates the non-restricted access area from the restricted access area. Each of gates 110 may be communicatively coupled to a network 140 via one or more wired and/or wireless connections. Transit system 100 may also include a transit server 142 and a central data store 144, each of which may be communicatively coupled to network 140. Transit server 142 may include a single or multiple processors, and may write, retrieve, or store data to central data store 144 or any of gates 110. Although embodiments herein are described in reference to transit systems, the restricted access area may correspond to an entertainment venue, a building, or any location involving metered access.

Figure 3:
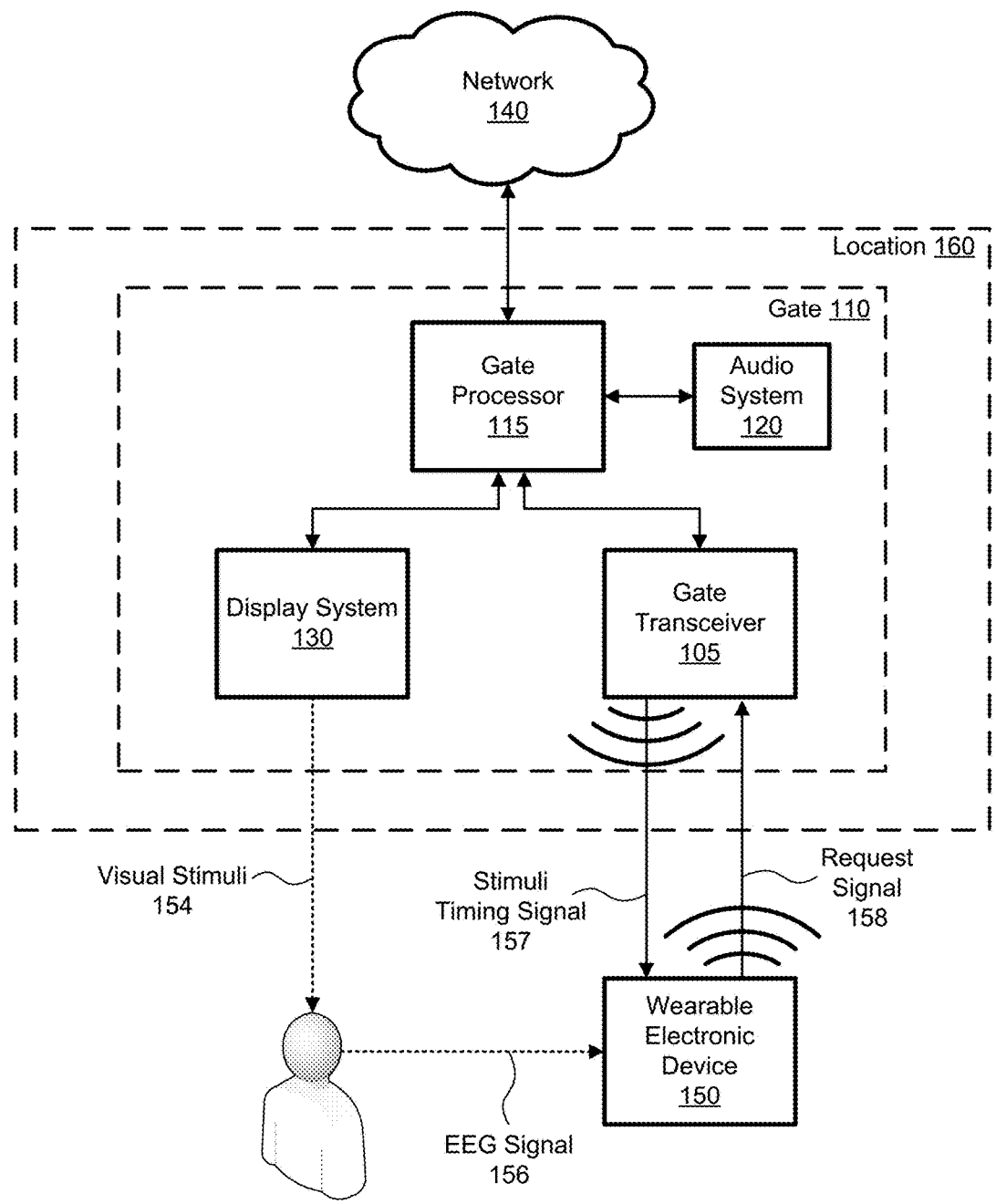
FIG. 3 illustrates a block diagram showing the interaction between various components of a transit system, according to some embodiments of the present disclosure.

FIG. 3 illustrates a block diagram showing the interaction between various components of transit system 100, according to some embodiments of the present disclosure. A holder (i.e., wearer) of wearable electronic device 150 may be a transit user of transit system 100 (i.e., customer or a potential customer of transit system 100) and may be inside or outside location 160 when wearable electronic device 150 communicates with one or more components of transit system 100. For example, the transit user may be inside or outside location 160 when the transit user views visual stimuli 154 and an EEG signal 156 is detected by wearable electronic device 150. As another example, wearable electronic device 150 may be inside or outside location 160 when a request signal 158 is transmitted by wearable electronic device 150 and is received by gate transceiver 105.

Gate 110 may be used as an entry point into transit system 100 (i.e., a restricted access area of transit system 100) and may, as illustrated in reference to FIG. 1, include a pair of gate cabinets defining a pathway from a non-restricted access area to a restricted access area. One of ordinary skill in the art will recognize that gate 110 can vary in appearance and functionality. Among other possible components, gate 110 may include a gate transceiver 105 for wirelessly communicating with wearable electronic device 150, an audio system 120 for outputting audio stimuli or for giving verbal instructions on using any of the components of gate 110, a display system 130 for displaying visual stimuli 154 or for giving instructions on using any of the components of gate 110, and a gate processor 115 for controlling the functionality of gate 110. One of skill in the art will recognize that barriers associated with gate 110 would open up to allow the holder of wearable electronic device 150 passage upon a successful communication between gate transceiver 105 and wearable electronic device 150.

Gate processor 115 may be in communication with each of gate transceiver 105, audio system 120, display system 130, as well as with network 140. Gate processor 115 may include a single or multiple processors and an associated memory. Gate processor 115 may provide the messaging presented on display system 130. Gate processor 115 may generate the messages to be displayed on display system 130 or receive the message to be displayed from any number of sources over network 140. Gate processor 115 may also generate the messages broadcast from audio system 120 or receive the message to be broadcast from any number of sources over the network 140. Gate processor 115 may communicate with gate transceiver 105 and may determine if the information contained in request signal 158 allows passage or may send the information in request signal 158 over network 140 to transit server 142 to make the determination.

Display system 130 may be any system capable of outputting visual stimuli 154 viewable by the transit user, including a digital display, a projector, a holographic image generator, and the like. Visual stimuli 154 may be generated and outputted by display system 130 or, in other embodiments, may be generated by gate processor 115 and subsequently outputted by display system 130. In some embodiments, display system 130 is configured to output visual stimuli 154 only when it is determined that a transit user is within a threshold distance of gate 110 (e.g., within location 160). In some embodiments, display system 130 continuously or periodically outputs visual stimuli 154 while gate 110 is powered on.

In addition to outputting/displaying visual stimuli 154, display system 130 may display a message for the transit user that wearable electronic device 150 is not in the correct place and can identify to the holder of wearable electronic device 150 where to correctly place wearable electronic device 150 to allow proper detection of EEG signal 156 and/or proper communication with gate transceiver 105. In other embodiments display system 130 can display any manner of other messages including instructions for using gate 110, instructions for using transit system 100, and advertising. In some embodiments, gate 110 may include a media reader that requires contact with the object to be read.

In some embodiments, EEG signal 156 is the resulting signal when the electrical activity of the brain is measured or detected by a sensor placed on or near the transit user's head. In some embodiments, wearable electronic device 150 includes one or more electrodes that are physically touching the transit user's head (e.g., scalp). When the transit user views visual stimuli 154, EEG signal 156 may exhibit certain patterns or characteristics that may be analyzed by wearable electronic device 150 to determine that the transit user is viewing visual stimuli 154. In some instances, visual stimuli 154 may change while the transit user is viewing and while the EEG signal 156 is being repeatedly detected by wearable electronic device 150. In such instances, the instant in time that a change is detected in EEG signal 156 may be compared with the instant in time that a change occurred in visual stimuli 154. In some embodiments, gate transceiver 105 may wirelessly transmit a stimuli timing signal 157 to wearable electronic device 150 that includes timing information for visual stimuli 154.

Gate transceiver 105 may engage in two-way communication with wearable electronic device 150 or, in some embodiments, gate transceiver 105 may be configured to only receive incoming wireless signals, such as request signal 158. Communication between gate transceiver 105 and wearable electronic device 150 may include any communication technology employing electromagnetic wireless signals. For example, the two devices may communicate using near-field communication (NFC), BLE, radio-frequency identification (RFID), and the like. In some embodiments, gate transceiver 105 may include an RFID reader and wearable electronic device 150 may include an RFID tag. The RFID tag may be passive, active, or battery-assisted passive. Active RFID tags have on-board batteries and periodically or constantly transmit wireless signals with identifying information. Battery-assisted passive RFID tags have small batteries on board and are activated when they are near an RFID reader. Passive RFID tags lack on-board batteries and are instead energized by the wireless signals received from RFID readers. In some embodiments, gate transceiver 105 includes an omni-directional antenna configured to repeatedly transmit stimuli timing signal 157 throughout at least a portion of location 160.

Wearable electronic device 150 may include (directly or indirectly via e.g., information linking to an external location) an amount of units which may be used to access transit system 100. For example, passage through different routes within transit system 100 may cause different amounts of units to be deleted from wearable electronic device 150 (or from the external location). In some embodiments, transit server 142 or some external processor may cause some portion of the amount of units to be held as unavailable. When a portion of units is held as unavailable, that portion may not be used for other purposes outside transit system 100 such that the portion is locked from usage. In one particular implementation, the amount of units may correspond to money (e.g., a cash amount) usable for financial transactions such as purchase of a fare within transit system 100.

Figure 4:
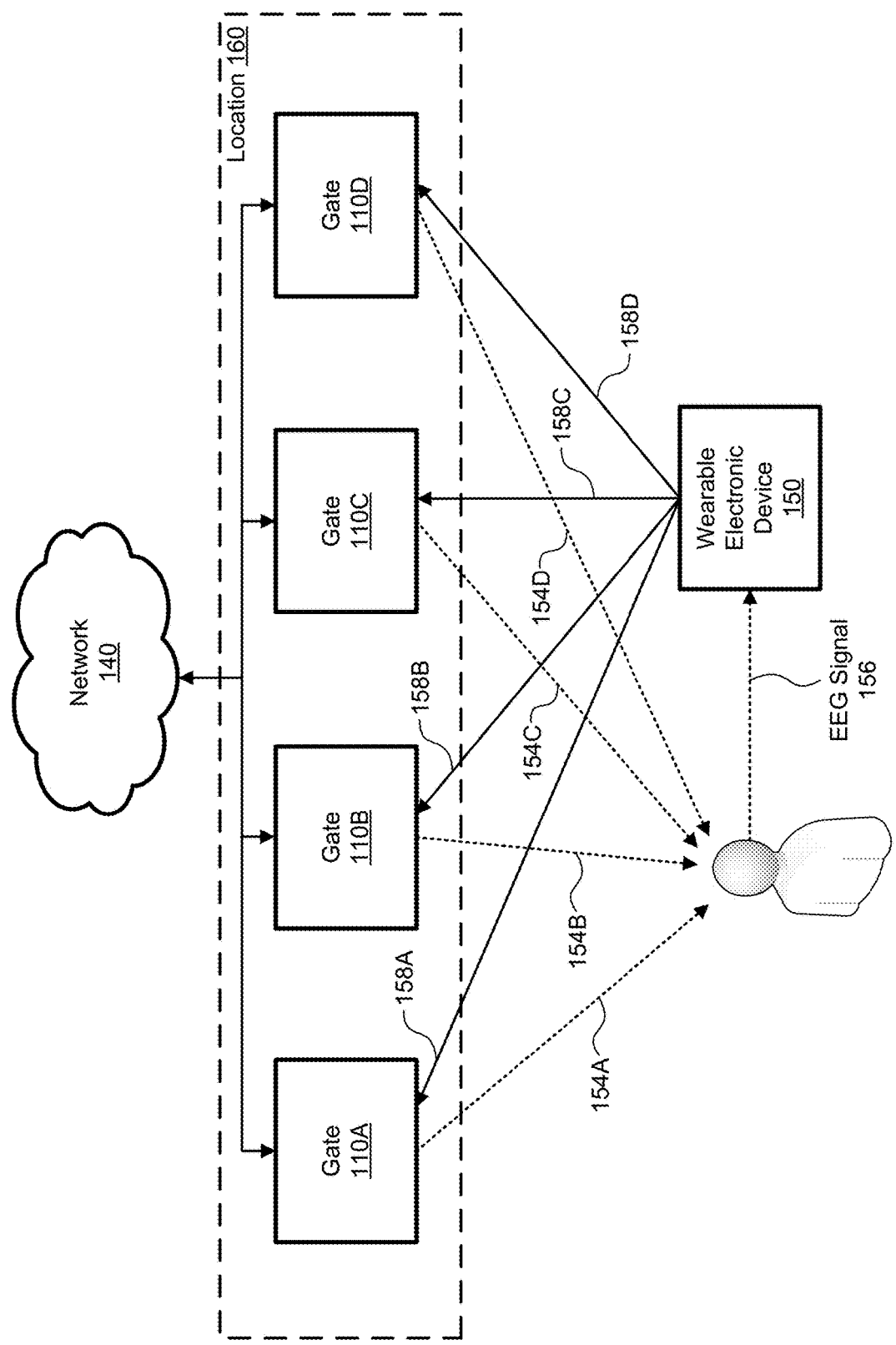
FIG. 4 illustrates a transit location including four gates, each having display systems outputting visual stimuli, according to some embodiments of the present disclosure.

FIG. 4 illustrates a block diagram of a particular embodiment of the present invention in which transit location 160 includes four gates 110 having display systems 130 outputting different visual stimuli 154. For example, visual stimuli 154A may include an identical animation to visual stimuli 154B that is temporally offset by, e.g., 1 or 2 seconds. Alternatively, visual stimuli 154A may include a completely different animation or image than visual stimuli 154B. In some embodiments, display systems 130 are positioned directly on the side of their corresponding gates 110, as illustrated in FIG. 1. In other embodiments, display systems 130 need not be positioned directly on or proximate to gates 110. For example, transit location 160 may include a central monitor that outputs each of visual stimuli 154 and may provide indicators below each visual stimuli 154 indicating which gate 110 corresponds to which visual stimuli 154. This allows a first transit user to look at visual stimuli 154A when he/she is walking towards gate 110A and a second transit user to look at visual stimuli 154B when he/she is walking towards gate 110B, etc.

After detecting EEG signal 156, wearable electronic device 150 may analyze EEG signal 156 to determine which of gates 110 the transit user is attempting to enter through. After determining which of gates 110 the transit user is attempting to enter through (i.e., the requested gate), wearable electronic device 150 may send request signal 158 to the requested gate only. Alternatively, or additionally, wearable electronic device 150 may modify request signal 158 to identify the requested gate and may send request signal 158 to each of gates 110. Each of gates 110 may then analyze request signal 158 to determine whether the requested gate is another gate or the current gate. If the requested gate matches the current gate, then the current gate may allow the transit user to access transit system 100 by, for example, opening a gate or turnstile.

Figure 5:
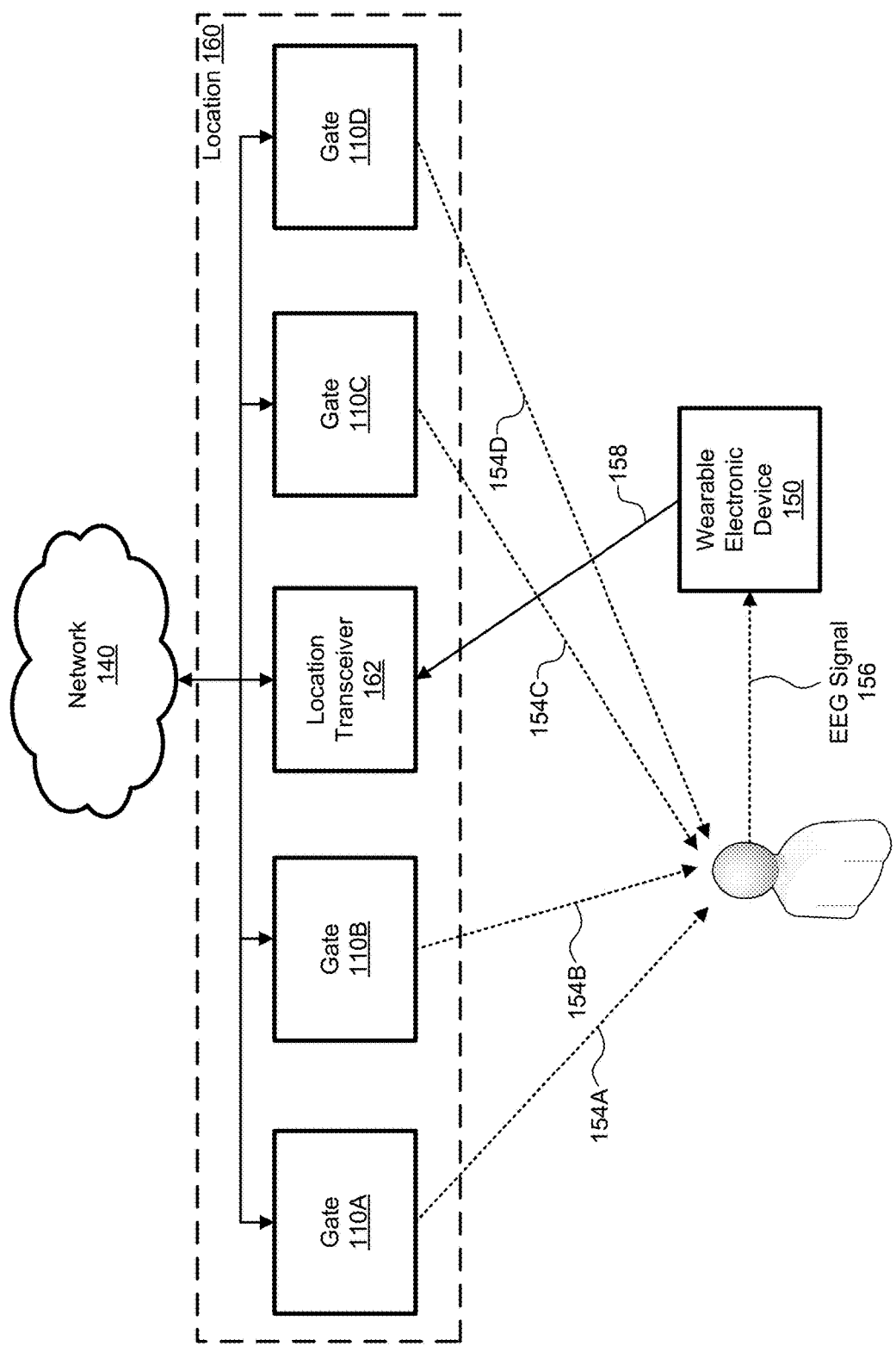
FIG. 5 illustrates a transit location including four gates and a location transceiver, according to some embodiments of the present disclosure.

FIG. 5 illustrates a block diagram of an alternative embodiment in which a location transceiver 162 conducts some or all of the wireless communication in place of gate transceivers 105. For example, location transceiver 162 may be configured to transmit stimuli timing signal 157 and receive request signal 158. Location transceiver 154 may be communicatively coupled with each of gates 110 and may be located within transit location 160 so as to be in a close proximity to transit users as they approach gates 110. Upon receiving request signal 158 from wearable electronic device 150, location transceiver 162 may analyze request signal 158 to determine which of gates 110 is the requested gate. After determining the requested gate, location transceiver 162 may forward request signal 158 in its entirety to the requested gate.

Figure 6:
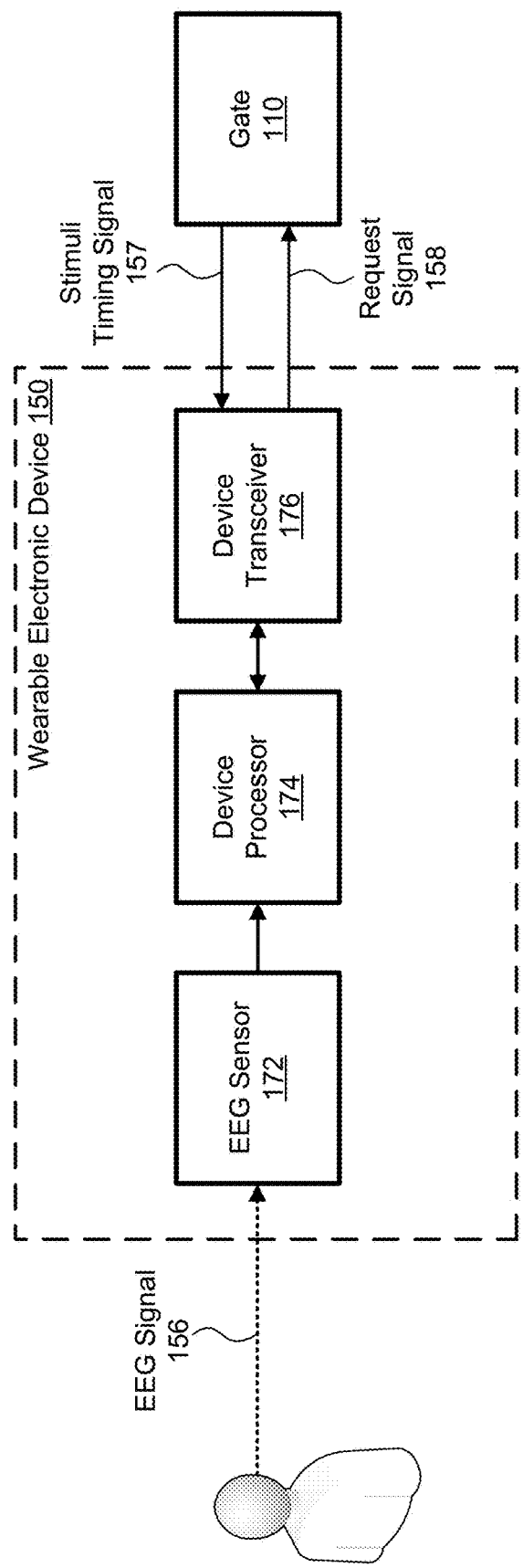
FIG. 6 illustrates a block diagram of a wearable electronic device, according to some embodiments of the present disclosure.

FIG. 6 illustrates a block diagram of wearable electronic device 150, according to some embodiments of the present disclosure. Wearable electronic device 150 may include an EEG sensor for detecting EEG signal 156 corresponding to the transit user. EEG sensor 172 may include a voltage sensor and an electrode that may come in physical contact with the transit user's head. EEG sensor 172 may be configured to detect different frequency bands associated with the electrical activity of the transit user's brain, such as the delta band (<4 Hz), the theta band (>4 Hz and <8 Hz), the alpha band (>8 Hz and <14 Hz) and the beta band (>14 Hz). In some embodiments, EEG sensor 172 may be configured to detect only the electrical activity in the beta band as it is related to active thinking. In other embodiments, all frequency bands may be monitored and used for analysis.

Wearable electronic device 150 may include a device processor 174 for receiving and analyzing EEG signal 156 and for generating request signal 158. Device processor 174 may also receive and analyze stimuli timing signal 157, prior to or concurrently with generating request signal 158. Wearable electronic device 150 may include a device transceiver 176 for transmitting and/or receiving wireless signals from gate 110. In some embodiments, device transceiver 176 only includes a transmitter such that stimuli timing signal 157 is not received by wearable electronic device 150. In such embodiments, other characteristics of EEG signal 156 may be analyzed to determine that the transit user is attempting to enter transit system 100 through gate 110, such as a gate-specific and/or user-specific signature in EEG signal 156.

Figure 7:
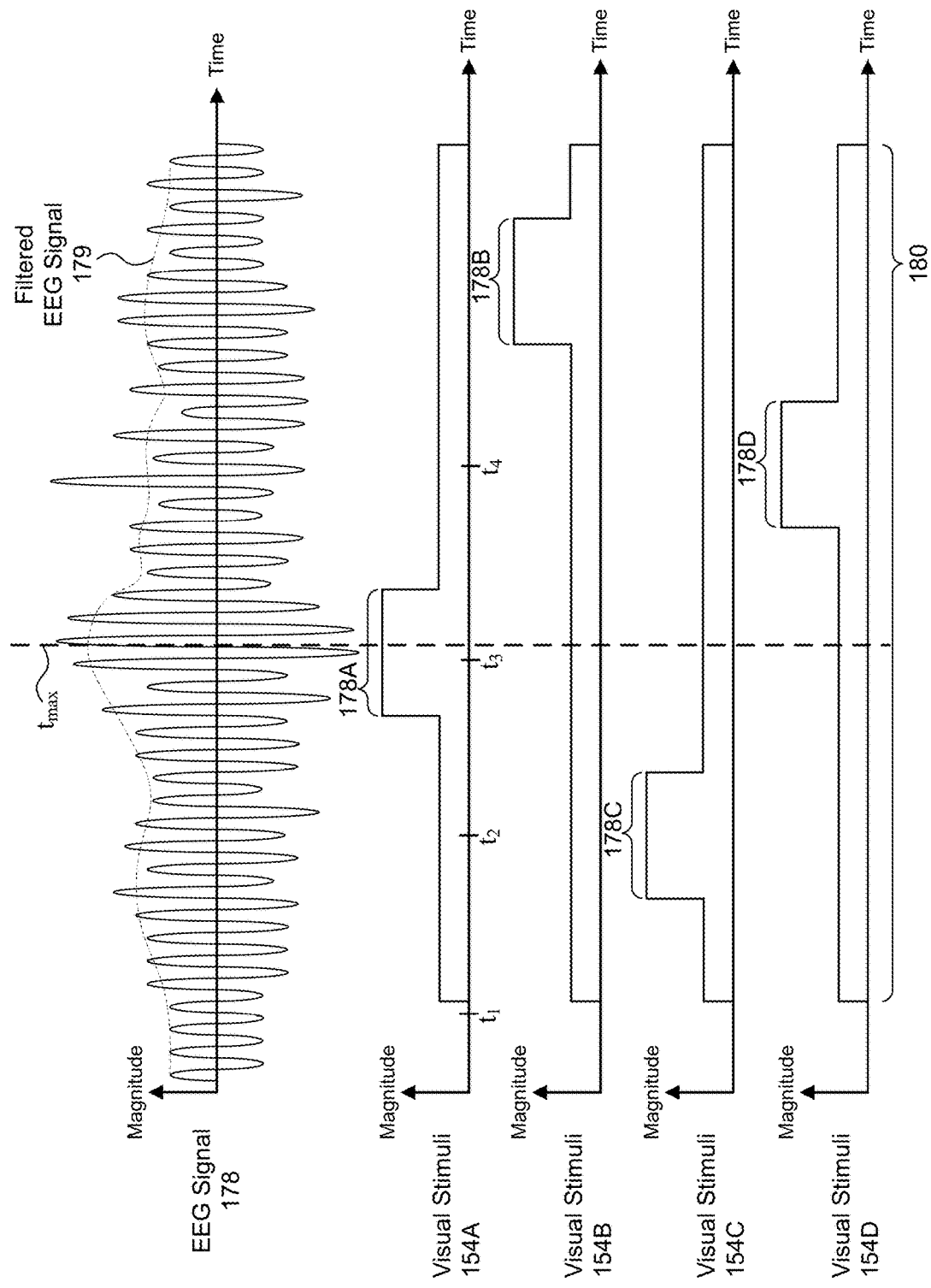
FIG. 7 illustrates an example of the analysis performed by a device processor in determining which gate a transit user is attempting to enter a transit system through, according to some embodiments of the present disclosure.

FIG. 7 illustrates an example of the analysis performed by device processor 174 in determining which gate the transit user is attempting to enter transit system 100 through. The magnitude of EEG signal 178 is plotted in the upper portion of FIG. 7 as a function of time. Although EEG signal 178 is shown as having both positive and negative values, in some embodiments EEG signal 178 may be only positive or only negative. Furthermore, EEG signal 178 may also include phase information that is useful for the analysis. As described previously, EEG signal 178 is available to device processor 174 using EEG sensor 172.

In the lower portion of FIG. 7, magnitude signals of visual stimuli 154 are plotted as a function of time. The time axis for each of the plots shown in FIG. 7 may correspond to each other such that comparisons may be made along any vertical line. Magnitude signals of visual stimuli 154 may correspond to various features of the displayed information. For example, the magnitude of visual stimuli 154 may be proportional to movement, brightness, color, vertical or horizontal placement of the displayed information, etc. In one particular implementation, the magnitude of visual stimuli 154 is proportional to the speed of a circle moving horizontally across visual stimuli 154 such that higher magnitudes correlate with higher velocities of the circle. In another implementation, the magnitude of visual stimuli 154 is proportional to the brightness of visual stimuli 154 such that higher magnitudes correlate with brighter images/animations. In another implementation, the magnitude of visual stimuli 154 is proportional to the frequency of a blinking light animation such that higher magnitudes correlate with higher blinking frequencies. Other possibilities are contemplated.

The plotted magnitudes of visual stimuli 154 shown in FIG. 7 may be available to device processor 174 through one of two approaches. In the first approach, the information may be contained in stimuli timing signal 157 such that wearable electronic device 150 may receive the information when the transit user approaches transit location 160. The advantages of this approach is that only a small amount of information needs to be transmitted wirelessly to reconstruct the magnitude signals due to the simplicity of the signals. For example, the magnitude signal of visual stimuli 154A can be recreated with four time values (time of first step up, time of second step up, time of first step down, and time of second step down) and two magnitude values (magnitude of first step and magnitude of second step). The remaining magnitude signals of visual stimuli 154B, 154C, and 154D may be recreated with even fewer values given their similarity to visual stimuli 154A. In some embodiments, the magnitude signals are defined by time ranges 178 (the time range of the maximum magnitude) and an interrogation time range 180 (the time range of non-zero magnitude). Time ranges 178 may be defined by a single value (starting time, ending time, some arbitrary middle time) when time ranges 178 have a known duration, or by two values (starting time and ending time, or starting time and duration, etc.).

In the second approach, the magnitude signals of visual stimuli 154 may be stored within wearable electronic device 150 and aligned with an internal clock as the transit user approaches transit location 160. For example, wearable electronic device 150 may be programmed for a particular transit location or a particular transit system with pre-known visual stimuli 154. As another example, wearable electronic device 150 may include a library of different magnitude signals of visual stimuli 154 that may be selectable by the transit user.

In the example shown in FIG. 7, device processor 174 may determine that the transit user is attempting to enter transit system 100 through gate 110A by performing the following steps. First, device processor 174 filters EEG signal 178 to generate a filtered EEG signal 179, which may, in some embodiments, be a time-averaged version of EEG signal 178 or an envelope of the oscillating EEG signal. Second, device processor 174 determines a critical time $t_{max}$ at which filtered EEG signal 179 (or EEG signal 178) exhibits a maximum value. Critical time $t_{max}$ has a restraint of being within interrogation time range 180. Third, device processor 174 identifies which of time ranges 178 includes critical time $t_{max}$. If none of time ranges 178 includes critical time $t_{max}$, then the steps are repeated with additional data. Because critical time $t_{max}$ is within time range 178A, device processor 174 determines that transit user is attempting to enter transit system 100 through gate 110A.

Figure 8:
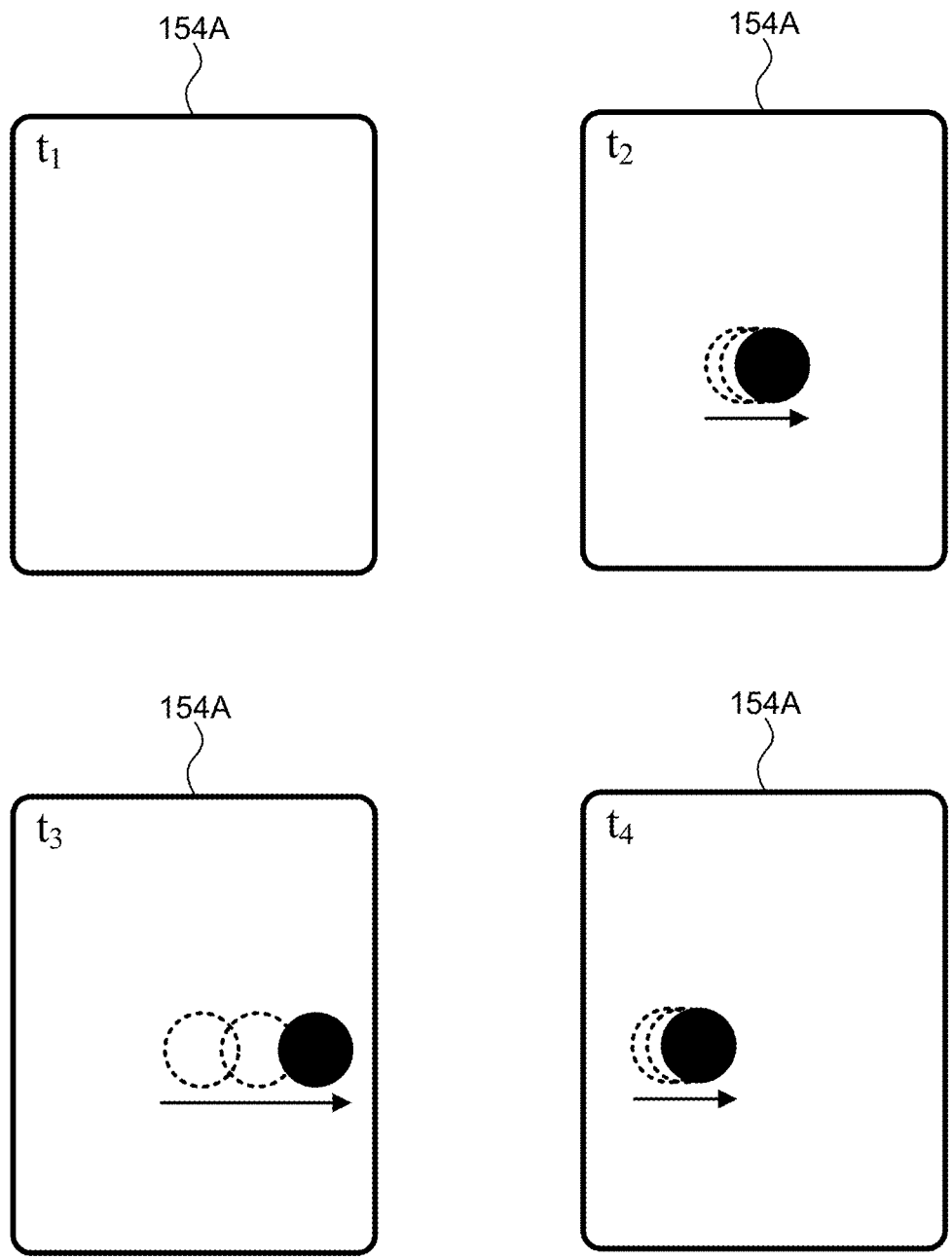
FIG. 8 illustrates four examples of visual stimuli at four instants in time, according to some embodiments of the present disclosure.

FIG. 8 illustrates four examples of visual stimuli 154A at four instants in time, corresponding to the magnitude signal for visual stimuli 154A shown in FIG. 7. At time $t_1$, visual stimuli 154A is blank and may be set to a default neutral image. At time $t_2$, visual stimuli 154A shows a circle moving horizontally at a low speed. When the circle reaches the right edge of the screen, it wraps around and appears at the left edge of the screen. At time $t_3$, visual stimuli 154A shows the circle moving horizontally at a high speed, the high speed being greater than the low speed. At time $t_4$, visual stimuli 154A shows the circle moving horizontally at the low speed. In this manner, the higher speed of the circle at time $t_3$ may cause the viewer (i.e., the transit user) to exhibit greater brain electrical activity at certain frequency bands than for lower speeds of the circle.

Figure 9:
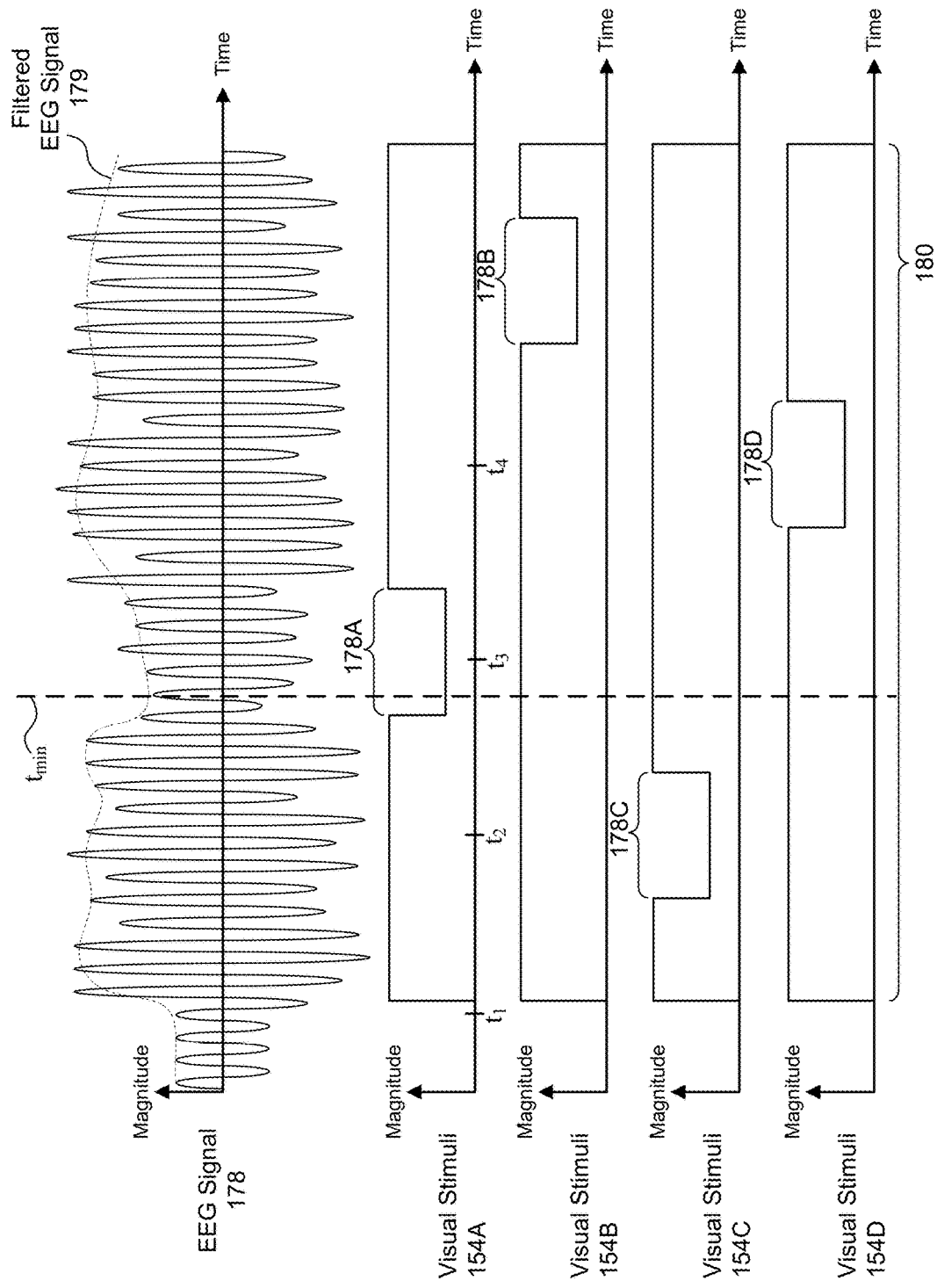
FIG. 9 illustrates an example of the analysis performed by a device processor in determining which gate a transit user is attempting to enter a transit system through, according to some embodiments of the present disclosure.

FIG. 9 illustrates an example of the analysis performed by device processor 174 in determining which gate the transit user is attempting to enter transit system 100 through. The magnitude of EEG signal 178 is plotted in the upper portion of FIG. 9 as a function of time, and magnitude signals of visual stimuli 154 are plotted as a function of time in the lower portion of FIG. 9. The time axis for each of the plots shown in FIG. 9 may correspond to each other such that comparisons may be made along any vertical line.

In the example shown in FIG. 9, device processor 174 may determine that the transit user is attempting to enter transit system 100 through gate 110A by performing the following steps. First, device processor 174 filters EEG signal 178 to generate a filtered EEG signal 179. Second, device processor 174 determines a critical time $t_{min}$ at which filtered EEG signal 179 (or EEG signal 178) exhibits a minimum value, critical time $t_{min}$ having a restraint of being within interrogation time range 180. Third, device processor 174 identifies which of time ranges 178 includes critical time $t_{min}$. If none of time ranges 178 includes critical time $t_{min}$, then the steps are repeated with additional data. Because critical time $t_{min}$ is within time range 178A, device processor 174 determines that transit user is attempting to enter transit system 100 through gate 110A.

Figure 10:
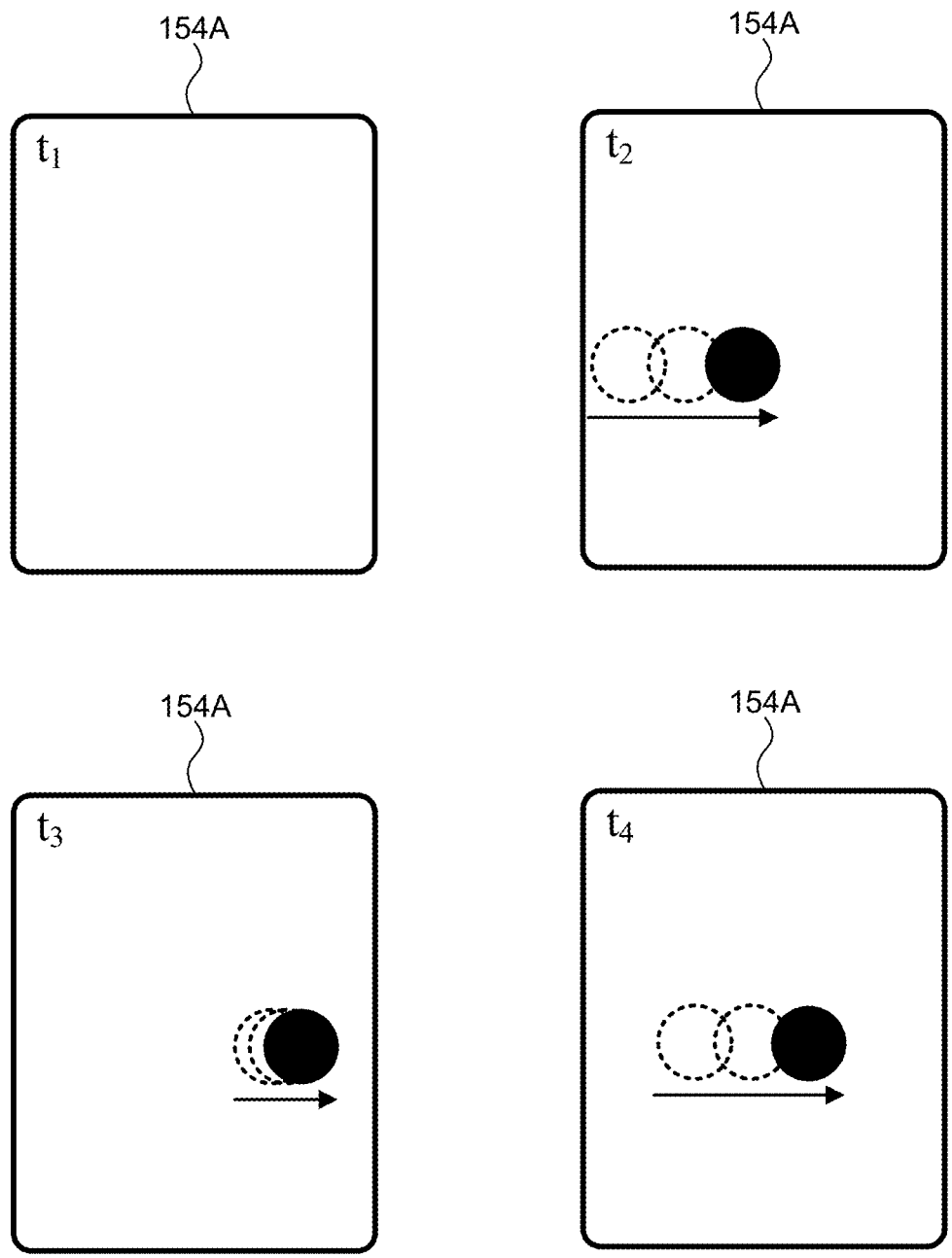
FIG. 10 illustrates four examples of visual stimuli at four instants in time, according to some embodiments of the present disclosure.

FIG. 10 illustrates four examples of visual stimuli 154A at four instants in time, corresponding to the magnitude signal for visual stimuli 154A shown in FIG. 9. At time $t_1$, visual stimuli 154A is blank and may be set to a default neutral image. At time $t_2$, visual stimuli 154A shows a circle moving horizontally at a high speed. When the circle reaches the right edge of the screen, it wraps around and appears at the left edge of the screen. At time $t_3$, visual stimuli 154A shows the circle moving horizontally at a low speed. At time $t_4$, visual stimuli 154A shows the circle moving horizontally at the high speed. In this manner, the lower speed of the circle at time $t_3$ may cause the viewer (i.e., the transit user) to exhibit lesser brain electrical activity at certain frequency bands than for higher speeds of the circle.

Figure 11:
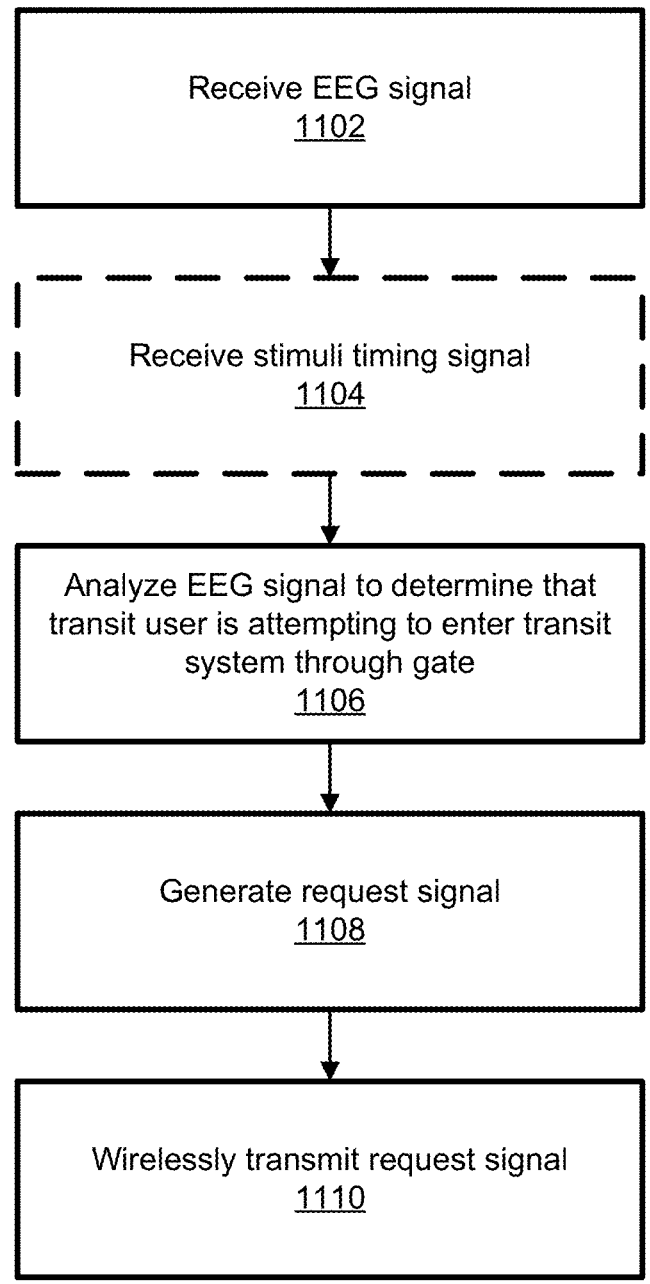
FIG. 11 illustrates a method of using EEG for enabling access to a transit system, according to some embodiments of the present disclosure.

FIG. 11 illustrates a method 1100 of using EEG for enabling access to a transit system, according to some embodiments of the present disclosure. Steps of method 1100 need not be performed in the order shown, and one or more steps may be omitted during performance of method 1100. In some embodiments, each of the steps of method 1100 are performed by wearable electronic device 150, or some component within wearable electronic device 150 such as device processor 174. In some embodiments, steps of method 1100 are performed by gate 110 in combination with wearable electronic device 150.

At step 1102, EEG signal 156 corresponding to a transit user is received by wearable electronic device 150. In some instances, EEG signal 156 is received by device processor 174 from EEG sensor 172. EEG signal 156 may be detected by EEG sensor 172 using one or more electrodes in physical contact with the transit user's head. In some embodiments, EEG signal 156 is the resulting signal when the electrical activity of the brain is measured or detected by EEG sensor 172. When the transit user is viewing visual stimuli 154, EEG signal 156 may be based at least in part on visual stimuli 154. In some embodiments, EEG signal 156 may be repeatedly received while wearable electronic device 150 is powered on or, in other embodiments or in the same embodiments, EEG signal 156 is received in response to wearable electronic device 150 receiving stimuli timing signal 157 (i.e., step 1102 may be performed in response to performance of step 1104).

At step 1104, stimuli timing signal 157 is received by wearable electronic device 150. In some instances, stimuli timing signal 157 may be wirelessly transmitted from gate transceiver 105 (i.e., gate 110) to device transceiver 176 (i.e., wearable electronic device 150), and may be subsequently routed/sent to device processor 174. Stimuli timing signal 157 may be repeatedly broadcast by gate 110 such that wearable electronic device 150 may determine that the transit user is approaching transit location 160 when stimuli timing signal 157 is first received. In some embodiments, stimuli timing signal 157 is transmitted by location transceiver 162 which may be communicatively coupled to a plurality of gates 110.

Stimuli timing signal 157 may include information about visual stimuli 154 that allows wearable electronic device 150 to analyze EEG signal 156 with different analytics than would be possible without the information. In some embodiments, stimuli timing signal 157 includes time range 178 indicating the period of time at which visual stimuli 154 exhibits a decreased magnitude or an increased magnitude. When transit location 160 includes multiple gates 110, stimuli timing signal 157 may include multiple time ranges 178 indicating different periods of time at which different visual stimuli 154 exhibit decreased magnitudes or increased magnitudes.

Time ranges 178 for different gates 110 may partially overlap or may have no overlap, depending on the embodiment. Stimuli timing signal 157 may also include interrogation time range 180 indicating the period of time at which visual stimuli 154 has a non-zero magnitude.

At step 1106, EEG signal 156 is analyzed by wearable electronic device 150 to determine that the transit user is attempting to enter transit system 100 through a particular gate.

In some instances, device processor 174 determines that the transit user is attempting to enter transit system 100 through a particular gate based on EEG signal 156 and stimuli timing signal 157. For example, device processor 174 may determine a critical time at which EEG signal 156 exhibits a minimum magnitude or a maximum magnitude, and may be compare the critical time to time ranges 178. If the critical time is within one of time ranges 178, then device processor 174 may determine that the corresponding gate is the particular gate the transit user is attempting to enter through. If the critical time is within none or more than one of time ranges 178, then method 1100 may return to step 1102 to receive a new EEG signal.

In some embodiments, EEG signal 156 may be analyzed to determine whether it contains one or more user characteristics corresponding to the transit user. For example, the transit user may train wearable electronic device 150 by repeatedly viewing visual stimuli 154 while wearable electronic device 150 is in a training mode and is being worn by the transit user. In this manner, wearable electronic device 150 is able to learn and recognize user characteristics within EEG signal 156 over time. Because different transit users may have different user characteristics, wearable electronic device 150 may be transferred and used by different transit users, and wearable electronic device 150 may be able to identify the transit user and determine which visual stimuli 154 the transit user is viewing. Other possibilities are contemplated.

At step 1108, request signal 158 is generated by wearable electronic device 150. In some instances, request signal 158 is generated by device processor 174. Request signal 158 may identify the transit user and may indicate that the transit user is attempting to enter transit system 100 through the particular gate. Accordingly, in some embodiments the only information contained in request signal 158 may be an identifier for the transit user (e.g., name, transit account number) and an identifier for the particular gate (e.g., gate number). In some embodiments, request signal 158 may include EEG signal 156 so that gate 110 may verify (or determine) the identity of the user and the particular gate.

At step 1110, request signal 158 is wirelessly transmitted by wearable electronic device 150 to gate 110. In some instances, request signal 158 is wirelessly transmitted by device transceiver 176 to gate transceiver 105. Alternatively or additionally, request signal 158 may be transmitted by device transceiver 176 to location transceiver 162 and subsequently sent to one or more of gates 110. In response to receiving request signal 158, gate 110 may determine whether the transit user is permitted to access transit system 100 by, for example, determining whether an account balance linked to the transit user has sufficient funds, determining whether the transit user has a transit pass, determining whether the transit user is included in a list of authorized transit users, and the like. In some embodiments, gate 110 may send a communication to transit server 142 to determine whether the transit user is permitted to access transit system 100. Upon determining that the transit user is permitted to enter, gate 110 may cause a barrier to be removed and may output an indication on display system 130 that the transit user is permitted to enter.

Figure 12:
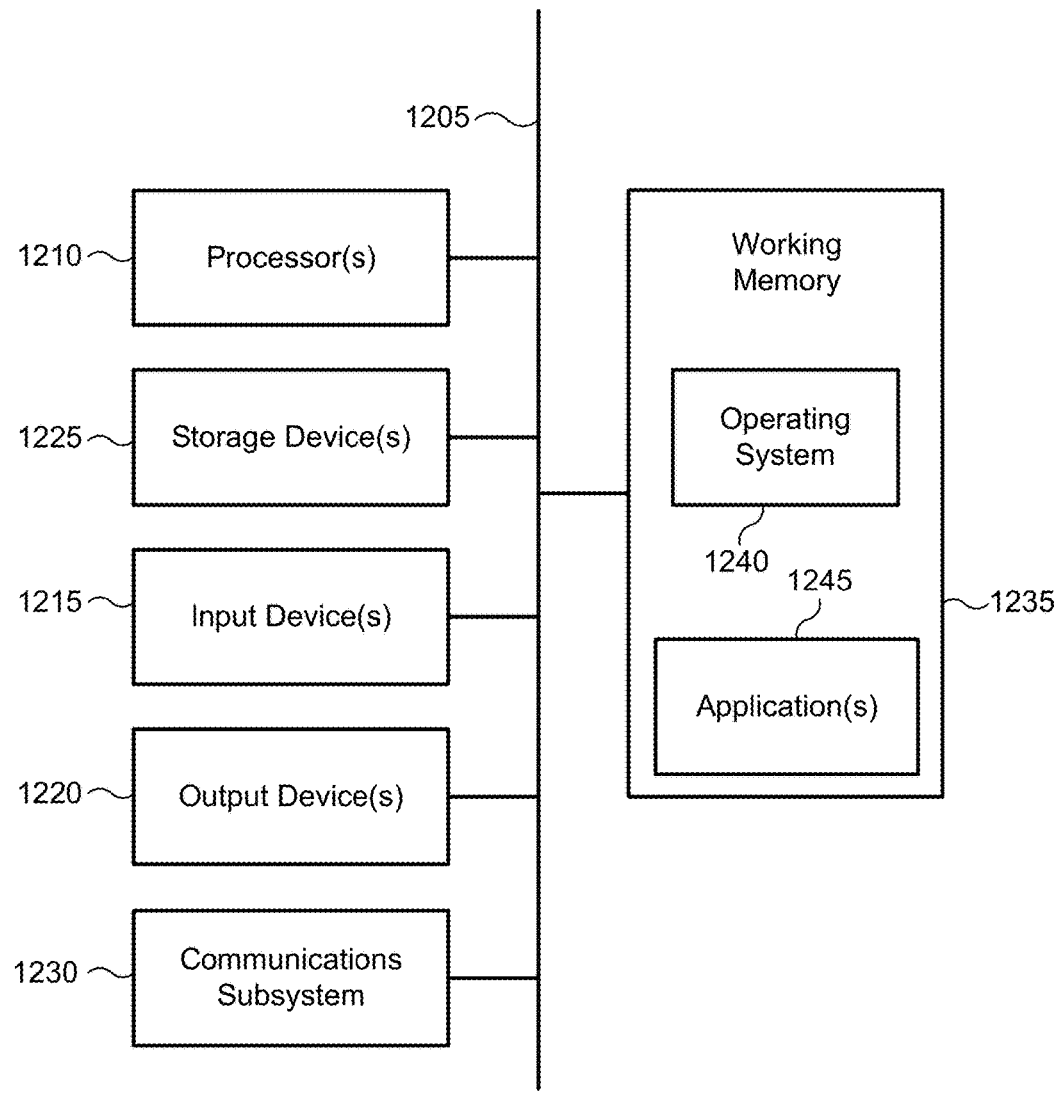
FIG. 12 illustrates a simplified computer system, according to some embodiments of the present disclosure.

FIG. 12 illustrates a simplified computer system 1200, according to some embodiments of the present disclosure. Computer system 1200 as illustrated in FIG. 12 may be incorporated into devices such as location transmitter 154, wearable electronic device 150, gate transceiver 105, and transit server 142 as described herein. FIG. 12 provides a schematic illustration of one embodiment of computer system 1200 that can perform some or all of the steps of the methods provided by various embodiments. It should be noted that FIG. 12 is meant only to provide a generalized illustration of various components, any or all of which may be utilized as appropriate. FIG. 12, therefore, broadly illustrates how individual system elements may be implemented in a relatively separated or relatively more integrated manner.

Computer system 1200 is shown comprising hardware elements that can be electrically coupled via a bus 1205, or may otherwise be in communication, as appropriate. The hardware elements may include one or more processors 1210, including without limitation one or more general-purpose processors and/or one or more special-purpose processors such as digital signal processing chips, graphics acceleration processors, and/or the like; one or more input devices 1215, which can include without limitation a mouse, a keyboard, a camera, and/or the like; and one or more output devices 1220, which can include without limitation a display device, a printer, and/or the like.

Computer system 1200 may further include and/or be in communication with one or more non-transitory storage devices 1225, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

Computer system 1200 might also include a communications subsystem 1230, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 1230 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 1230. In other embodiments, a portable electronic device, e.g. the first electronic device, may be incorporated into computer system 1200, e.g., an electronic device as an input device 1215. In some embodiments, computer system 1200 will further comprise a working memory 1235, which can include a RAM or ROM device, as described above.

Computer system 1200 also can include software elements, shown as being currently located within the working memory 1235, including an operating system 1240, device drivers, executable libraries, and/or other code, such as one or more application programs 1245, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 12, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code may be stored on a non-transitory computer-readable storage medium, such as the storage device(s) 1225 described above. In some cases, the storage medium might be incorporated within a computer system, such as computer system 1200. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by computer system 1200 and/or might take the form of source and/or installable code, which, upon compilation and/or installation on computer system 1200 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as computer system 1200 to perform methods in accordance with various embodiments of the technology. According to a set of embodiments, some or all of the procedures of such methods are performed by computer system 1200 in response to processor 1210 executing one or more sequences of one or more instructions, which might be incorporated into the operating system 1240 and/or other code, such as an application program 1245, contained in the working memory 1235. Such instructions may be read into the working memory 1235 from another computer-readable medium, such as one or more of the storage device(s) 1225. Merely by way of example, execution of the sequences of instructions contained in the working memory 1235 might cause the processor(s) 1210 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using computer system 1200, various computer-readable media might be involved in providing instructions/code to processor(s) 1210 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 1225. Volatile media include, without limitation, dynamic memory, such as the working memory 1235.

Common forms of physical and/or tangible computer-readable media include, for example, a floppy disk, a flexible disk, hard disk, magnetic tape, or any other magnetic medium, a CD-ROM, any other optical medium, punch-cards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 1210 for execution. Merely by way of example, the instructions may initially be carried on a magnetic disk and/or optical disc of a remote computer. A remote computer might load the instructions into its dynamic memory and send the instructions as signals over a transmission medium to be received and/or executed by computer system 1200.

The communications subsystem 1230 and/or components thereof generally will receive signals, and the bus 1205 then might carry the signals and/or the data, instructions, etc. carried by the signals to the working memory 1235, from which the processor(s) 1210 retrieves and executes the instructions. The instructions received by the working memory 1235 may optionally be stored on a non-transitory storage device 1225 either before or after execution by the processor(s) 1210.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a schematic flowchart or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A wearable electronic device for enabling access to a transit system, the wearable electronic device comprising:
    an electroencephalography (EEG) sensor configured to detect an EEG signal resulting from a transit user viewing either a first visual stimulus displayed by a first display mounted to a first gate or a second visual stimulus displayed by a second display mounted to a second gate;
    a device transmitter configured to transmit wireless signals to a gate receiver; and
    a device processor configured to perform operations including:
        receiving the EEG signal from the EEG sensor;
        analyzing the EEG signal to determine whether the transit user is attempting to enter the transit system through the first gate or the second gate;
        in response to determining that the transit user is attempting to enter the transit system through the first gate, generating a request signal, wherein the request signal identifies the transit user and indicates that the transit user is attempting to enter the transit system through the first gate; and
        wirelessly transmitting, using the device transmitter, the request signal to the gate receiver.

2. The wearable electronic device of claim 1, wherein analyzing the EEG signal to determine that the transit user is attempting to enter the transit system through the first gate includes:
    determining a first time range at which the first visual stimulus exhibits a first decreased magnitude or a first increased magnitude;
    determining a critical time at which the EEG signal exhibits a minimum magnitude or a maximum magnitude; and
    determining that the critical time is within the first time range.

3. The wearable electronic device of claim 2, wherein analyzing the EEG signal to determine that the transit user is attempting to enter the transit system through the first gate further includes:
    determining a second time range at which the second visual stimulus exhibits a second decreased magnitude or a second increased magnitude; and
    determining that the critical time is not within the second time range.

4. The wearable electronic device of claim 3, wherein the operations further include:
    receiving, from a first transmitter communicatively coupled to the first gate, the first time range; and
    receiving, from a second transmitter communicatively coupled to the second gate, the second time range.

5. The wearable electronic device of claim 3, wherein the operations further include:
    receiving, from a location transmitter communicatively coupled to the first gate and the second gate, the first time range and the second time range.

6. The wearable electronic device of claim 1, wherein the first gate allows the transit user to access the transit system upon reception of the request signal.

7. A method of using electroencephalography (EEG) for enabling access to a transit system, the method comprising:
    receiving an EEG signal from an EEG sensor of a wearable electronic device, wherein the EEG sensor is configured to detect the EEG signal resulting from a transit user viewing either a first visual stimulus displayed by a first display mounted to a first gate or a second visual stimulus displayed by a second display mounted to a second gate;
    analyzing the EEG signal to determine whether the transit user is attempting to enter the transit system through the first gate or the second gate;
    in response to determining that the transit user is attempting to enter the transit system through the first gate, generating a request signal, wherein the request signal identifies the transit user and indicates that the transit user is attempting to enter the transit system through the first gate; and
    wirelessly transmitting the request signal to a gate receiver.

8. The method of claim 7, wherein analyzing the EEG signal to determine that the transit user is attempting to enter the transit system through the first gate includes:
    determining a first time range at which the first visual stimulus exhibits a first decreased magnitude or a first increased magnitude;
    determining a critical time at which the EEG signal exhibits a minimum magnitude or a maximum magnitude; and
    determining that the critical time is within the first time range.

9. The method of claim 8, wherein analyzing the EEG signal to determine that the transit user is attempting to enter the transit system through the first gate further includes:
    determining a second time range at which the second visual stimulus exhibits a second decreased magnitude or a second increased magnitude; and
    determining that the critical time is not within the second time range.

10. The method of claim 9, further comprising:
    receiving, from a first transmitter communicatively coupled to the first gate, the first time range; and
    receiving, from a second transmitter communicatively coupled to the second gate, the second time range.

11. The method of claim 9, further comprising:
receiving, from a location transmitter communicatively coupled to the first gate and the second gate, the first time range and the second time range.

12. The method of claim 7, wherein the first gate allows the transit user to access the transit system upon reception of the request signal.

13. A non-transitory computer-readable medium comprising instructions that, when executed by a processor, cause the processor to perform operations comprising:
receiving an electroencephalography (EEG) signal from an EEG sensor of a wearable electronic device, wherein the EEG sensor is configured to detect the EEG signal resulting from a transit user viewing either a first visual stimulus displayed by a first display mounted to a first gate or a second visual stimulus displayed by a second display mounted to a second gate;
analyzing the EEG signal to determine whether the transit user is attempting to enter a transit system through the first gate or the second gate;
in response to determining that the transit user is attempting to enter the transit system through the first gate, generating a request signal, wherein the request signal identifies the transit user and indicates that the transit user is attempting to enter the transit system through the first gate; and
wirelessly transmitting the request signal to a gate receiver.

14. The non-transitory computer-readable medium of claim 13, wherein analyzing the EEG signal to determine that the transit user is attempting to enter the transit system through the first gate includes:
determining a first time range at which the first visual stimulus exhibits a first decreased magnitude or a first increased magnitude;
determining a critical time at which the EEG signal exhibits a minimum magnitude or a maximum magnitude; and
determining that the critical time is within the first time range.

15. The non-transitory computer-readable medium of claim 14, wherein analyzing the EEG signal to determine that the transit user is attempting to enter the transit system through the first gate further includes:
determining a second time range at which the second visual stimulus exhibits a second decreased magnitude or a second increased magnitude; and
determining that the critical time is not within the second time range.

16. The non-transitory computer-readable medium of claim 15, wherein the operations further include:
receiving, from a first transmitter communicatively coupled to the first gate, the first time range; and
receiving, from a second transmitter communicatively coupled to the second gate, the second time range.

17. The non-transitory computer-readable medium of claim 15, wherein the operations further include:
receiving, from a location transmitter communicatively coupled to the first gate and the second gate, the first time range and the second time range.

* * * * *